(12) United States Patent
Tanaka et al.

(10) Patent No.: US 10,406,126 B2
(45) Date of Patent: Sep. 10, 2019

(54) ALDH2 ACTIVATOR

(71) Applicant: Eisai R&D Management Co., Ltd., Bunkyo-ku, Tokyo (JP)

(72) Inventors: Keigo Tanaka, Tsukuba (JP); Tasuku Ishida, Tsukuba (JP); Masayuki Miyano, Tsukuba (JP); Raku Shinkyo, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/260,350

(22) Filed: Jan. 29, 2019

(65) Prior Publication Data

US 2019/0231720 A1    Aug. 1, 2019

(30) Foreign Application Priority Data

Jan. 31, 2018  (JP) .................. 2018-015512

(51) Int. Cl.
| C07C 233/73 | (2006.01) |
| C07C 235/60 | (2006.01) |
| A61K 31/166 | (2006.01) |
| A61P 7/06 | (2006.01) |
| A61P 29/00 | (2006.01) |
| A61P 19/10 | (2006.01) |

(52) U.S. Cl.
CPC .............. *A61K 31/166* (2013.01); *A61P 7/06* (2018.01); *A61P 19/10* (2018.01); *A61P 29/00* (2018.01); *C07C 233/73* (2013.01); *C07C 235/60* (2013.01)

(58) Field of Classification Search
CPC ........................... C07C 233/73; C07C 235/60
See application file for complete search history.

(56) References Cited

FOREIGN PATENT DOCUMENTS

| JP | 2010523476 | 7/2010 |
| JP | 2012087116 | 5/2012 |
| JP | 2016514154 | 5/2016 |
| WO | WO 2008/112164 | 9/2008 |
| WO | WO 2014/160185 | 10/2014 |

OTHER PUBLICATIONS

Registry No. 1181487-96-6, File Registry on STN, Entered STN: Sep. 9, 2009.*
Guengerich, "Mechanisms of Drug Toxicity and Relevance to Pharmaceutical Development," Drug Metabolism and Pharmacokinetics, 2011, 26:3-14.
Mittal et al., "Pharmacological activation of aldehyde dehydrogenase 2 promotes osteoblast differentiation via bone morphogenetic protein-2 and induces bone anabolic effect," Toxicology and Applied Pharmacology, 2017, 316:63-73.
Miyaji et al., "In vitro evaluation of the potential for drug-induced toxicity based on $^{35}$S-labeled glutathione adduct formation and daily dose," Bioanalysis, 2012, 4(3):263-269.
Nakayama et al., "A Zone Classification System for Risk Assessment of Idiosyncratic Drug Toxicity Using Daily Dose and Covalent Binding," Drug Metabolism and Disposition, 2009,. 37(9):1970-1977.
Zhu et al., "Pretreatment with the ALDH2 agonist Alda-1 reduces intestinal injury induced by ischaemia and reperfusion in mice," Clinical Science, 2017, 131:1123-1136.
International Search Report in International Application No. PCT/JP2019/002955, dated Mar. 5, 2019, 5 pages.

* cited by examiner

*Primary Examiner* — Rebecca L Anderson
(74) *Attorney, Agent, or Firm* — Fish & Richardson P.C.

(57) ABSTRACT

The present invention provides a compound represented by formula (1):

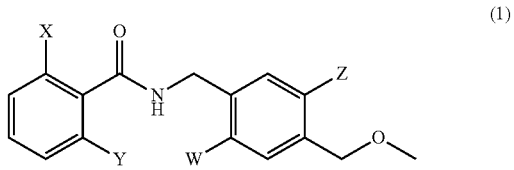

(1)

or pharmaceutically acceptable salt thereof, wherein
X and Y are the same or different from each other and represent a hydrogen atom, a halogen atom, a $C_{1-6}$ alkyl group, or a $C_{1-6}$ alkoxy group, wherein the $C_{1-6}$ alkoxy group may be substituted with a $C_{1-6}$ alkoxy group, and
Z and W are the same or different from each other and represent a hydrogen atom, a halogen atom, or a $C_{1-6}$ alkyl group.

5 Claims, No Drawings

ALDH2 ACTIVATOR

CROSS-REFERENCE TO RELATED APPLICATION

This application claims the benefit of Japanese patent application No. 2018-015512 filed on Jan. 31 2018, the disclosure of which is herein incorporated by reference in its entirety.

TECHNICAL FIELD

The present invention relates to an ALDH2 activator.

BACKGROUND

Aldehyde dehydrogenase 2 (ALDH2) is an enzyme that detoxifies endogenous or exogenous aldehydes harmful to a living body, such as acetaldehyde and 4-hydroxynonenal, by oxidizing them.

Thus, ALDH2-activating compounds are expected to have various pharmaceutical effects as listed in Patent Literature 1. Among the ALDH2-activating compounds, N-[(2H-1,3-benzodioxol-5-yl)methyl]-2,6-dichlorobenzamide (hereinafter referred to as "Alda-1") described in Patent Literature 2 has been reported to have various pharmaceutical effects in the non-clinical studies (for example, Non Patent Literature 1 and Non Patent Literature 2).

However, Alda-1 has challenging problems for its clinical development. Hie problems include production of reactive metabolites. Reactive metabolites are generally known to potentially cause serious blood toxicity and liver damage (Non Patent Literature 3). Clozapine, which is an antipsychotic agent and is an example of drugs causing serious blood toxicity and liver damage, has been reported to produce reactive metabolites abundantly m in vitro tests using matrix from human liver (Non Patent Literatures 4, 5). As demonstrated in Test Example 2 below, Alda-1 is a compound that produces reactive metabolites as much as clozapine.

Therefore, a compound that has an effect of activating ALDH2 and produces a smaller amount of reactive metabolites is desirable.

CITATION LIST

Patent Literature

[Patent Literature 1] WO 2014/160185
[Patent Literature 2] WO 2008/112164

Non Patent Literature

[Non Patent Literature 1] Qiankun Zhu et al., "Pretreatment with the ALDH2 agonist Alda-1 reduces intestinal injury induced by ischaemia and reperfusion in mice", Clinical Science, 131, 1123-1136, 2017.
[Non Patent Literature 2] Monika Mittal et al., "Pharmacological activation of aldehyde dehydrogenase 2 promotes osteoblast differentiation via bone morphogenetic protein-2 and induces bone anabolic effect", Toxicology and Applied Pharmacology, 316, 63-73, 2017.
[Non Patent Literature 3] F. Peter Guengerich "Mechanisms of Drug Toxicity and Relevance to Pharmaceutical Development", Drug Metabolism and Pharmacokinetics, 26, 3-14, 2011.
[Non Patent Literature 4] Shintaro Nakayama et al., "A Zone Classification System for Risk Assessment of Idiosyncratic Drug Toxicity Using Daily Dose and Covalent Binding", Drug Metabolism and Disposition, 37, 1970-1977, 2009.
[Non Patent Literature 5] Yoshihiro Miyaji et al., "In vitro evaluation of the potential for drug-induced toxicity based on 35S-labeled glutathione adduct formation and daily dose", Bioanalysis, 4,263-269, 2012.

SUMMARY

A problem to be solved by the present invention is to provide a compound that has an effect of activating ALDH2 and produces a small amount of reactive metabolites.

The present inventors have made every effort to achieve the present invention.

Namely, the present invention relates to the following [1] to [32]:

[1] A compound represented by formula (1):

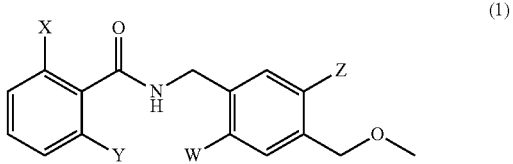

or a pharmaceutically acceptable salt thereof wherein X and Y are the same or different from each other and represent a hydrogen atom, a halogen atom, a $C_{1-6}$ alkyl group, or a $C_{1-6}$ alkoxy group, wherein the $C_{1-6}$ alkoxy group may be substituted with a $C_{1-6}$ alkoxy group, and Z and W are the same or different from each other and represent a hydrogen atom, a halogen atom, or a $C_{1-6}$ alkyl group.

[2] The compound or a pharmaceutically acceptable salt thereof according to [1], wherein the halogen atom is a fluorine atom, a chlorine atom, or a bromine atom.
[3] The compound or a pharmaceutically acceptable salt thereof according to [1] or [2], wherein the $C_{1-6}$ alkyl group is a methyl group or an isopropyl group.
[4] The compound or a pharmaceutically acceptable salt thereof according to any one of [1] to [3], wherein X is a hydrogen atom, a fluorine atom, a chlorine atom, a bromine atom, a methyl group, an isopropyl group, or a methoxymethoxy group.
[5] The compound or a pharmaceutically acceptable salt thereof according to any one of [1] to [4], wherein Y is a chlorine atom, a bromine atom, or a methyl group.
[6] The compound or a pharmaceutically acceptable salt thereof according to any one of [1] to [5], wherein Z is a hydrogen atom, a fluorine atom, or a methyl group.
[7] The compound or a pharmaceutically acceptable salt thereof according to any one of [1] to [6], wherein W is a hydrogen atom or a fluorine atom.
[8] A compound selected from:
(1) 2,6-dichloro-N-{[3-fluoro-4-(methoxymethyl)phenyl]methyl}benzamide;
(2) 2,6-dichloro-N-{[3,6-difluoro-4-(methoxymethyl)phenyl]methyl}benzamide;
(3) 2,6-dichloro-N-[4-(methoxymethyl)benzyl]benzamide,
(4) 2,6-dichloro-{[4-(methoxymethyl)-3-methylphenyl]methyl}benzamide;

(5) 2-bromo-6-chloro-N-{[3-fluoro-4-methoxymethyl)phenyl]methyl}benzamide,
(6) 2-chloro-N-{[3-fluoro-4-(methoxymethyl)phenyl]methyl}benzamide,
(7) 2-bromo-N-{[3-fluoro-4-(methoxymethyl)phenyl]methyl}benzamide,
(8) 2-bromo-6-fluoro-N-{[3-fluoro-4-(methoxymethyl)phenyl]methyl}benzamide,
(9) 2-chloro-N-{[3-fluoro-4-(methoxymethyl)phenyl]methyl}-6-(methoxymethyl)benzamide,
(10) 2-chloro-6-fluoro-N-{[3-fluoro-4-(methoxymethyl)phenyl]methyl}benzamide,
(11) N-{[3-fluoro-4-(methoxymethyl)phenyl]methyl}-2,6-dimethylbenzamide,
(12) 2-chloro-N-[3-fluoro-4-(methoxymethyl)benzyl]-6-isopropylbenzamide, and
(13) 2,6-difluoro-N-{[3-fluoro-4-(methoxymethyl)phenyl]methyl}benzamide or a pharmaceutically acceptable salt thereof.
[9] 2,6-dichloro-N-{[3-fluoro-4-(methoxymethyl)phenyl]methyl}benzamide represented by the formula:

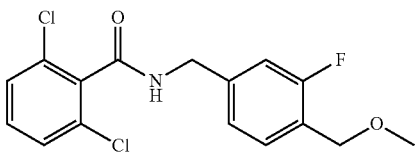

or a pharmaceutically acceptable salt thereof.
[10] 2,6-dichloro-N-{[4-(methoxymethyl)-3-methylphenyl]methyl}benzamide represented by the formula;

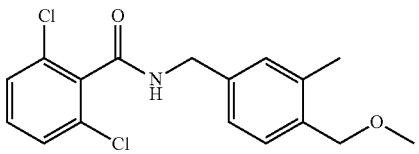 [SMILES: COCc1ccc(CNC(=O)c2c(Cl)cccc2Cl)cc1C]

or a pharmaceutically acceptable salt thereof.
[11] 2-bromo-6-fluoro-N-{[3-fluoro-4-(methoxymethyl)phenyl]methyl}benzamide represented by the formula:

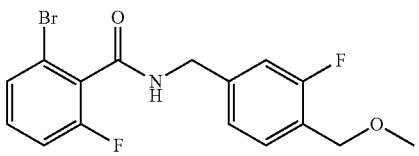 [SMILES: COCc1ccc(CNC(=O)c2c(F)cccc2Br)cc1F]

or a pharmaceutically acceptable salt thereof.
[12] A pharmaceutical composition comprising the compound or a pharmaceutically acceptable salt thereof according to any one of [1] to [11].
[13] The pharmaceutical composition according to [12], wherein the pharmaceutical composition is a therapeutic agent for radiodermatitis.
[14] The pharmaceutical composition according to [12], wherein the pharmaceutical composition is a therapeutic agent for osteoporosis.
[15] The pharmaceutical composition according to [12], wherein the pharmaceutical composition is a therapeutic agent for Fanconi anemia.
[16] The pharmaceutical composition according to [12], wherein the pharmaceutical composition is a therapeutic agent for inflammatory pain.
[17] The pharmaceutical composition according to [12], wherein the pharmaceutical composition is an ALDH2 activator.
[18] A method for treating radiodermatitis, comprising administering the compound or a pharmaceutically acceptable salt thereof according to any one of [1] to [11] to a patient in need thereof.
[19] A method for treating osteoporosis, comprising administering the compound or a pharmaceutically acceptable salt thereof according to any one of [1] to [11] to a patient in need thereof.
[20] A method for treating Fanconi anemia, comprising administering the compound or a pharmaceutically acceptable salt thereof according to any one of [1] to [11] to a patient in need thereof.
[21] A method for treating inflammatory pain, comprising administering the compound or a pharmaceutically acceptable salt thereof according to any one of [1] to [11] to a patient in need thereof.
[22] A method for activating ALDH2, comprising administering the compound or a pharmaceutically acceptable salt thereof according to any one of [1] to [11] to a patient in need thereof.
[23] The compound or a pharmaceutically acceptable salt thereof according to any one of [1] to [11] for use in the treatment of radiodermatitis.
[24] The compound or a pharmaceutically acceptable salt thereof according to any one of [1] to [11] for use in the treatment of osteoporosis.
[25] The compound or a pharmaceutically acceptable salt thereof according to any one of [1] to [11] for use in the treatment of Fanconi anemia.
[26] The compound or a pharmaceutically acceptable salt thereof according to any one of [1] to [ 11] for use in the treatment of inflammatory pain.
[27] The compound or a pharmaceutically acceptable salt thereof according to any one of [1] to [11] for use in the activation of ALDH2.
[28] Use of the compound or a pharmaceutically acceptable salt thereof according to any one of [1] to [11] for the manufacture of a therapeutic agent for radiodermatitis.
[29] Use of the compound or a pharmaceutically acceptable salt thereof according to any one of [1] to [11] for the manufacture of a therapeutic agent for osteoporosis.
[30] Use of the compound or a pharmaceutically acceptable salt thereof according to any one of [1] to [11] for the manufacture of a therapeutic agent for Fanconi anemia.
[31] Use of the compound or a pharmaceutically acceptable salt thereof according to any one of [1] to [11] for the manufacture of a therapeutic agent for inflammatory pain.
[32] Use of the compound or a pharmaceutically acceptable salt thereof according to any one of [1] to [11] for the manufacture of an ALDH2 activator.

DETAILED DESCRIPTION

The present invention provides a compound that has an effect of activating ALDH2 and produces a small amount of reactive metabolites. In other words, a compound according to the present invention has a potential use as an ALDH2 activator.

The present invention will be described in more detail below. The term "a compound according to the present invention" as used herein refers to a compound represented by formula (1) or a pharmaceutically acceptable salt thereof. A compound represented by formula (1) may be referred to as "compound (1)" as appropriate.

A compound according to the present invention has the structure as shown for the moiety with the conformation clearly defined in formula (1) whereas other moieties with the conformation that is not clearly defined may exist as stereoisomers which, may be either of the stereoisomers or a mixture thereof. At the same time, a compound according to the present invention, which can exist as polymorphic forms, is not limited to a particular crystal form only and may exist as any one of crystal forms or a mixture thereof. A compound according to the present invention includes an amorphous form, an anhydrate, and a solvate such as a hydrate.

The meanings of terms and symbols or the like as described herein will be illustrated and the present invention will be also described in more detail below.

The term "halogen atom" as used herein refers to a fluorine atom, a chlorine atom, a bromine atom, or an iodine atom.

The term "$C_{1-6}$ alkyl group" as used herein refers to a straight or branched alkyl group having 1 to 6 carbon atoms and specific examples thereof include a methyl group, an ethyl group, a 1-propyl group, a 2-propyl group, a 2-methyl-1-propyl group, a 2-methyl-2-propyl group, a 1-butyl group, a2-butyl group, a 1-pentyl group, a2-pentyl group, a3-pentyl group, a 1-hexyl group, a 2-hexyl group, and a 3-hexyl group.

The term "$C_{1-6}$ alkoxy group" as used herein refers to a group having an oxygen atom attached to the terminal of the "$C_{1-6}$ alkyl group" as defined above and specific examples thereof include a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 1-hexyloxy group, a 2-hexyloxy group, and a 3-hexyloxy group.

X in a compound represented by formula (1) is a hydrogen atom, a halogen atom, a $C_{1-6}$ alkyl group, or a $C_{1-6}$ alkoxy group, wherein the $C_{1-6}$ alkoxy group may be substituted with a $C_{1-6}$ alkoxy group. X is preferably a hydrogen atom, a fluorine atom a chlorine atom, a bromine atom, a methyl group, an isopropyl group, or a methoxymethoxy group.

Y in a compound represented by formula (1) is a hydrogen atom, a halogen atom, a $C_{1-6}$ alkyl group, or a $C_{1-6}$ alkoxy group, wherein the $C_{1-6}$ alkoxy group may be substituted with a $C_{1-6}$ alkoxy group. Y is preferably a chlorine atom, a bromine atom, or a methyl group.

Z in a compound represented by formula (1) is a hydrogen atom, a halogen atom, or a $C_{1-6}$ alkyl group and is preferably a hydrogen atom, a fluorine atom, or a methyl group.

W in a compound represented by formula (I) is a hydrogen atom, a halogen atom, or a $C_{1-6}$ alkyl group and is preferably a hydrogen atom or a fluorine atom.

The term "pharmaceutically acceptable salt" as used herein is not particularly limited as long as it can be formed with a compound represented by formula (1) and is pharmaceutically acceptable, and examples of the pharmaceutically acceptable salt include inorganic acid salts, organic acid salts, inorganic base salts, organic base salts, and acidic or basic amino acid salts.

Preferable examples of the inorganic acid salts include hydrochloride, hydrobromide, sulfate, nitrate, and phosphate, and preferable examples of the organic acid salts include carboxylates, such as acetate, succinate, fumarate, maleate, tartrate, citrate, lactate, stearate, benzoate, and mandelate; and sulfonates, such as methanesulfonate, ethanesulfonate, p-toluenesulfonate, and benzenesulfonate.

Preferable examples of the inorganic base salts include alkaline metal salts, such as sodium salt and potassium salt; alkaline-earth metal salts, such as calcium salt and magnesium salt; aluminum salt; and ammonium salt, and preferable examples of the organic base salts include diethyl amine salt, diethanolamine salt, meglumine salt, and N,N'-dibenzylethylenediamine salt.

Preferable examples of the acidic amino acid salts include aspartate and glutamate, and preferable examples of the basic amino acid salts include arginine salt, lysine salt, and omithine salt.

A Compound represented by formula (1) can be produced using methods described below. The methods for producing a compound represented by formula (1) are not limited to the methods and may be modified based on the common knowledge of those skilled in the art.

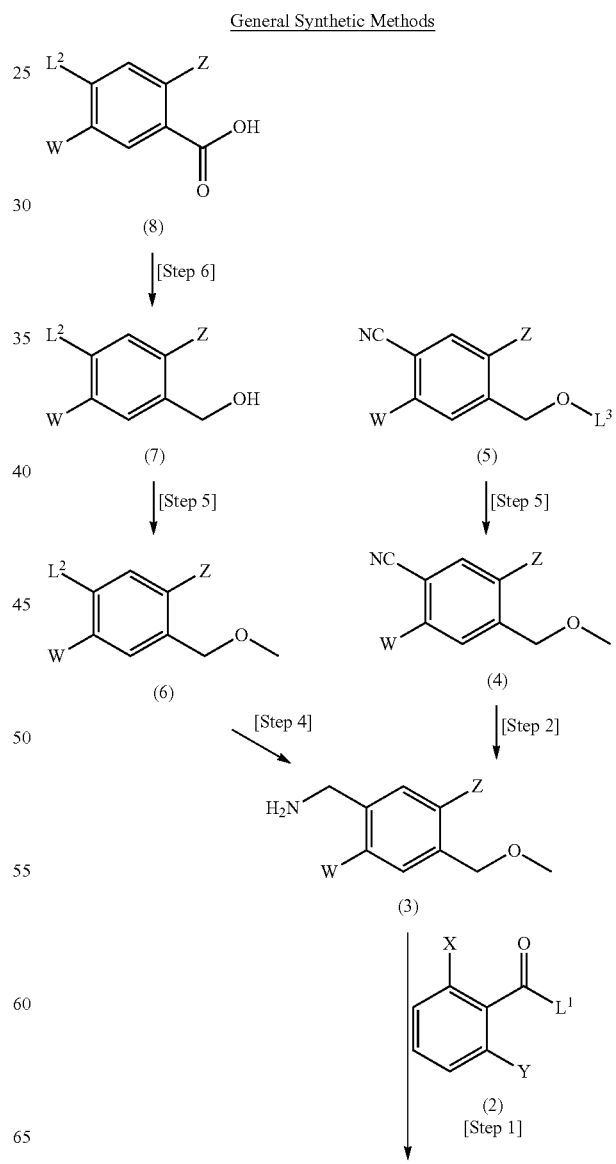

General Synthetic Methods

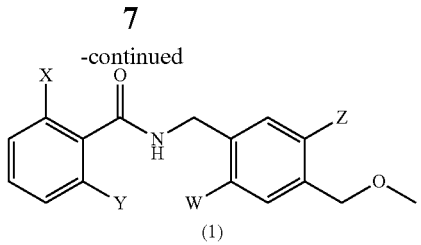

wherein X, Y, Z, and W are each as defined above, and L¹, L², and L³ are the same or different from one another and each represent a leaving group such as a hydroxy group or a halogen atom.

The method for producing compound (1) will be described below.

Step 1

In this step, compound (2) is reacted with compound (3) to give compound (1).

Compound (2) may be used directly from a commercially available product or produced from commercially available products using any known method. Moreover, compound (2) can be produced using the method in step A-1 below or the like.

Compound (3) may be used directly from a commercially available product or produced from commercially available products using any known method. Moreover, compound (3) can be produced using the methods described in the Production Examples in Examples below or in step 2 or step 4 below later or the like.

This step can be performed under conditions similar to commonly used conditions as described in the following literatures. Examples of known methods include methods described in J. Med. Chem., 34(1), 227-234 (1991) and J. Med. Chem., 37(7), 999-1014 (1994).

A solvent to be used in this reaction is not particularly limited as long as it can partly dissolve starting materials and do not inhibit the reaction, and examples of the solvent include tetrahydrofurane, 1,4-dioxane, ethyl acetate, methyl acetate, dichloromethane, chloroform, DMF, toluene, and xylenes. Condensing agents that can be used include CDI (N,N'-carbonyldiimidazole), Bop (1H-1,2,3-benzotriazol-1-yloxy(tri(dimethylamino))phosphonium hexafluorophosphate), WSC (1-ethyl-3-(3-dimethylaminopropyl)carbodiimide hydrochloride), DCC (N,N-dicyclohexylcarbodiimide), diethyl phosphoryl cyanide, and PyBOP (benzotriazol-1-yloxytris(pyrrolidino)phosphonium hexafluorophosphate).

Compound (2) can be used in an amount of from one equivalent relative to compound (3) to an excessive amount. An organic base such as triethylamine and diisopropylamine may optionally be added in an amount of from one equivalent relative to compound (3) to an excessive amount. The reaction temperature will vary depending on stalling materials and a solvent to be used and is preferably, but not particularly limited to, from an ice-cold temperature to the reflux temperature of the solvent. The reaction time is usually, but not particularly limited to, from 0.5 to 48 hours and preferably from 0.5 to 24 hours.

Acylation reaction, which is a method known to those skilled in the art, can be also used in this step. Examples of the base used in the acylation reaction include triethylamine, pyridine, potassium carbonate, and diisopropylethylamine.

The reaction temperature is usually, but not particularly limited to, from −78° C. to the reflux temperature of the solvent and preferably from −20° C. to room temperature.

A solvent to be used in the acylation reaction is not particularly limited as long as it does not inhibit the reaction and can partly dissolve starting materials, and examples of the solvent preferably include tetrahydrofurane, diethyl ether, toluene, and dichloromethane.

Step 2

In this step, cyano compound (4) is subjected to a reduction reaction to give compound (3).

This step is not particularly limited as long as it is a reduction method known to those skilled in the art, and examples of the reduction method include reduction by catalytic hydrogenation using lithium aluminum hydride or a mixture of lithium aluminum hydride and aluminum chloride, or a metallic catalyst, such as Raney nickel, palladium, platinum, or cobalt boride. Preferably, examples of the reduction method include a reduction reaction using alane prepared from aluminum chloride and lithium aluminum hydride.

Step 3

In this step, leaving group L³ of compound (5) is substituted with a methoxy group to give compound (4).

This reaction can be performed under conditions similar to the conditions typically used in a reaction in which a leaving group is converted to a methoxy group. Example of methoxylating agents include, but are not particularly limited to, sodium methoxide and a solution of sodium methoxide in methanol. A solvent to be used for the reaction is not particularly limited as long as it does not inhibit the reaction and can partly dissolve starting materials, and examples of the solvent preferably include methanol. The reaction temperature usually ranges from −78° C. to the reflux temperature of the solvent and preferably from 0° C. to the reflux temperature of the solvent. The reaction time is usually, but not particularly limited to, from 5 minutes to 48 hours and preferably from 5 minutes to 12 hours.

Step 4

In this step, leaving group L² of compound (6) is converted to a derivative of an aminomethyl group by a condensation reaction using a transition metal and subsequently a protecting group of the amine is deprotected to give compound (3).

Examples of aminomethylation conditions that can be performed include conditions similar to the reaction conditions as described in Org. Lett., 14(11), 2818-2821 (2012). Specifically, examples of organometallic catalysts to be used in this reaction preferably include, but are not particularly limited to, metallic catalysts such as palladium acetate (II), tris(dibenzylideneacetone)dipalladium(0), and (dibenzylideneacetone)palladium(0). The organometallic catalysts are used in an amount of from about 0.001 to 0.5 equivalent relative to starting materials. Examples of the aminomethyl derivative, which is a condensation partner, preferably include, bus are not particularly limited to, sodium [(1,3-dioxoisoindolin-2-yl)methyl]trifluoroborate. The aminomethyl derivative is typically used in an amount of, but not particularly limited to, from 1 to 5 equivalents relative to compound (6). A solvent to be used in this reaction is not particularly limited as long as it does not inhibit the reaction, and examples of the solvent can preferably include 1,4-dioxane, water, and a mixture thereof. Examples of ligands to be used preferably include, but are not particularly limited to, XPhos and SPhos. Examples of such bases or salts preferably include, but are not particularly limited to, lithium carbonate, sodium carbonate, potassium carbonate, and cesium carbonate. The reaction temperature is usually, but not particularly limited to, from an ice-cold temperature to the reflux temperature of the solvent and preferably, for example, from room temperature to the reflux temperature of the solvent. The reaction time is usually, but not particularly limited to, from 0.5 to 48 hours and preferably from 0.5 to 24 hours.

Subsequent deprotection of the protecting group on the amino group is performed under conditions which are not particularly limited when the protecting group is a phthalate group, but preferably, addition of deprotecting agents, including ethylenediamine and hydrazine hydrate, may produce an excellent result. Further addition of a solvent may produce an excellent result when the protecting group is a phthalate group. A solvent to be added is not particularly limited as long as it does not inhibit the reaction, and examples of the solvent preferably include methanol, ethanol, 1-propanol, 2-propanol, and 1-butanol. The reaction temperature is usually, but not particularly limited to, from an ice-cold temperature to the reflux temperature of the solvent and preferably, for example, from room temperature to the reflux temperature of the solvent. The reaction time is usually, but not particularly limited to, from 0.5 to 96 hours and preferably from 1 to 48 hours when the protecting group is a phthalate group.

Step 5

In this step, the hydroxy group of compound (7) is converted to a methoxy group to give compound (6).

This step can be performed under conditions similar to the conditions commonly used in a reaction where a hydroxy group is converted to a methoxy group. Examples of methylating agents preferably include, but are not particularly limited to, methyl iodide and dimethyl sulfate. Bases to be used are not particularly limited unless inhibiting the reaction, and examples of the bases preferably include sodium hydride. A solvent to be used in the reaction is not particularly limited as long as it does not inhibit the reaction and can partly dissolve starting materials, and examples of the solvent preferably include tetrahydrofurane, DMF, DMSO, and NMP. The reaction temperature is usually from −78° C. to the reflux temperature of the solvent and preferably from 0° C. to 50° C. The reaction time is usually, but not particularly limited to, from 5 minutes to 48 hours and preferably from 5 minutes to 12 hours.

Step 6

In this step, compound (8) is subjected to a reduction reaction to give compound (7).

Carboxylic acid compound (8) can be used in any method known to those skilled in the art to give alcohol compound (7). Examples of reducing agents to be used in the reaction include a borane dimethyl sulfide complex and a borane tetrahydrofurane complex. The reaction temperature is usually, but not particularly limited to, from −78° C. to the reflux temperature of the solvent and preferably from −20° C. to room temperature. A solvent to be used in the reaction is not particularly limited as long as it does not inhibit the reaction and can partly dissolve starting materials, and examples of the solvent preferably include tetrahydrofurane and diethyl ether.

Compound (2-1), which is Compound (2) wherein Y is a $C_{1-6}$ alkoxy group optionally substituted with a $C_{1-6}$ alkoxy group can be synthesized using the following method:

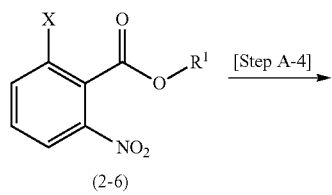

(2-6)

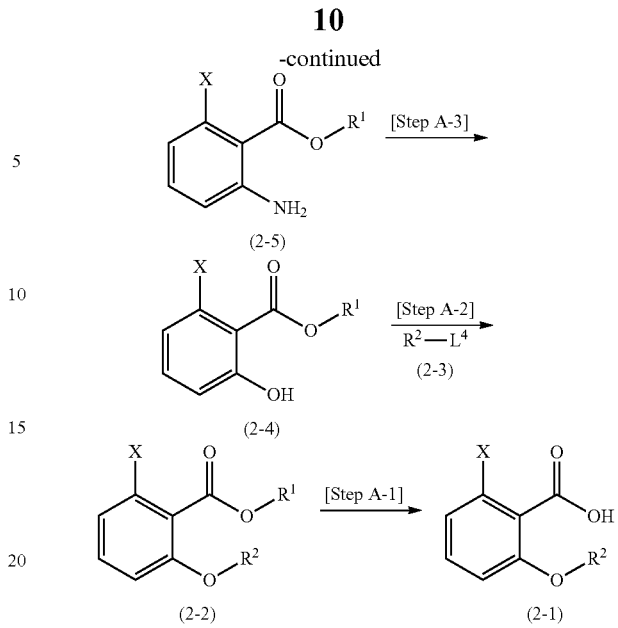

wherein X is as defined above; $L^4$ represents a leaving group as with $L^1$ to $L^3$ as described above; $R^1$ represents a $C_{1-6}$ alkyl group; and $R^2$ represents a $C_{1-6}$ alkoxy group optionally substituted with a $C_{1-6}$ alkyl group.

Compounds (2-1), (2-2), (2-3), (2-4), (2-5), and (2-6) to be used in this step may be used directly from commercially available products or produced from commercially available products using any method known to those skilled in the art or methods as described in the Production Examples in Examples.

Step A-1

In this step, the ester moiety of compound (2-2) is hydrolyzed to give compound (2-1).

A method for synthesizing compound (2-1) by hydrolyzing the ester moiety of compound (2-2) is a synthesis method known to those skilled in the art and examples of the method include, but are not particularly limited to, a reaction using a base or salt in an aqueous solvent. Examples of the base or salt to be used preferably include, but are not particularly limited to, lithium hydroxide or a hydrate thereof, sodium hydroxide, and potassium hydroxide. The solvent to be used in this reaction is not particularly limited as long as it does not inhibit the reaction, and examples of the solvent preferably include tetrahydrofurane, dioxane, methanol, ethanol, water, and a mixture thereof. The reaction temperature is usually, but not particularly limited to, from an ice-cold temperature to the reflux temperature of the solvent and preferably, for example, from room temperature to the reflux temperature of the solvent. The reaction time is usually, but not particularly limited to, from 0.5 to 48 hours and preferably from 0.5 to 24 hours.

Step A-2

In this step, the etherification reaction between compounds (2-3) and (2-4) is performed to give compound (2-2).

A method for synthesizing compound (2-2) by the etherification between compounds (2-3) and (2-4) is a synthesis method known to those skilled in the art, and for example, compound (2-3) is used m an amount of, but not particularly limited to, from 1 to 5 equivalents relative to compound (2-4). A solvent to be used in this reaction is not particularly limited as long as it does not inhibit the reaction, and examples of the solvent can preferably include tetrahydrofurane, DMF, DMSO, and NMP. Examples of bases or salts to be used preferably include, but are not particularly limited to, lithium carbonate, sodium carbonate, potassium carbonate, cesium carbonate, triethylamine, diisopropylethylamine, and sodium hydride. The reaction temperature is usually, but not particularly limited to, from an ice-cold temperature to the reflux temperature of the solvent, and preferably, for example, from room temperature to the reflux temperature of the solvent. The reaction time is usually, but not particularly limited to, from 0.5 to 48 hours, and preferably from 0.5 to 24 hours.

Step A-3

In this step, compound (2-4) is obtained from compound (2-5).

A method for synthesizing hydroxide compound (2-4) by Sandmeyer reaction using compound (2-5) can be performed under conditions similar to the commonly used conditions as described in the following literatures. This method can be performed under conditions similar to reaction conditions of known methods, for example, as described in J. Org. Chem, 42(12), 2053-2058 (1977) and J. Med. Chem, 47(4), 871-887 (2004). Examples of the method preferably include heating under reflux using sodium nitrite and sulfide acid in a water solvent.

Step A-4

In this step, compound (2-5) is obtained from compound (2-6).

A method for synthesizing compound (2-5) by reducing the nitro compound of compound (2-6) is a synthesis method known to those skilled in the art and examples of the method include catalytic hydrogenation using noble metal catalysts, such as Raney nickel, palladium, ruthenium, rhodium, and platinum; and a reduction reaction using a stoichiometric amount of iron(0), tin(II) chloride, or titanium(III) chloride. Examples of the method preferably include a reduction reaction with iron under neutral conditions using ammonium chloride.

After a reaction in each method or each step as described above, the target compound of each step can be collected from the reaction mixture in accordance with a conventional method.

The methods as described above are representative of methods for producing compound (1), but starting compounds and various reagents in the production of compound (1) may form their salts or exist as their solvate forms such as a hydrate, and may both vary depending on the starting materials or a solvent used, and are not particularly limited as long as they do not inhibit the reactions. A solvent to be used will also vary depending on stalling materials or reagents, and the solvent is not particularly limited as long as it does not inhibit the reactions and can partly dissolve the starting materials. When compound (1) is obtained as a free form, the free form of compound (1) can be converted, in accordance with a conventional method, to a salt or a solvate thereof that is acceptably formed.

When compound (1) is obtained as a salt or solvate, the salt or solvate can be converted to its free form in accordance with a conventional method.

Various isomers (such as geometrical isomer, optical, isomer, rotational isomer, stereoisomer, and tautomer) for compound (1) or its intermediate can be purified and isolated using conventional separation techniques, for example, crystallization, diastereomeric salt formation, enzymatic resolution, and different chromatographic methods (such as thin-layer chromatography, column chromatography, and gas chromatography).

Pharmaceutical compositions according to the present invention can be produced by combining a pharmaceutically acceptable additive with compound (1) or a pharmaceutically acceptable salt thereof. Pharmaceutical compositions according to the present invention can be produced according to a known method such as a method, tor example as described in General Rules for Preparations in The Japanese Pharmacopoeia, Sixteenth Edition.

Pharmaceutical compositions in accordance with to the present invention can be administered appropriately to a patient depending on their dosage forms.

The dosage of medicaments according to the present invention will typically vary depending on a symptom, age, sex, or body weight and may be an amount sufficient to have a desired effect. For example, a dosage of about 0.1 to 5000 mg (preferably 0.5 to 1000 mg) per day will be given as a single dose or 2 to 6 subdivided doses for a single day or a plurality of days for an adult.

A compound according to the present invention includes isotopically labeled compounds of compound (1), which are identical to compound (1) except that one or more atoms are replaced by an atom having an atomic mass or mass number different from the atomic mass or mass number usually found in nature. Examples of isotopes that can be incorporated into compound (I) include isotopes of hydrogen, carbon, nitrogen, oxygen, phosphorus, fluorine, iodine, and chlorine, such as $^{2}H$, $^{3}H$, $^{11}C$, $^{14}C$, $^{18}F$, $^{35}S$, $^{123}I$, and $^{125}I$.

Compound (1) or a pharmaceutically acceptable derivative (such as salt) thereof, which contains the aforementioned isotopes and/or oilier isotopes, are encompassed within the scope of the compounds according to the present invention. Isotopically-labeled compounds according to the present invention, for example, those into which radioactive isotopes such as $^{3}H$ and $^{14}C$ are incorporated, are useful in tissue distribution assays for a medicament or substrate. Isotopes $^{3}H$ and $^{14}C$ are believed to be useful due to their ease of preparation and detection. Isotopes $^{11}C$ and $^{18}F$ are believed to be useful for positron-emission tomography (PET) while isotope $^{125}I$ is believed to be useful for single photon emission computed tomography (SPECT). Isotopes $^{11}C$, $^{18}F$, and $^{125}I$ are all useful for brain imaging. Substitution with heavier isotopes such as $^{2}H$ can afford certain therapeutic advantages resulting from greater metabolic stability, for example, increased in vivo half-life or reduced dosage requirements and, hence, is believed to be useful in some circumstances. An isotopically labeled compound of compound (1) can equally be prepared by performing the procedures disclosed in the Examples section below using a readily available isotopically labeled reagent instead, of anon-isotopically labeled reagent.

Compound (1) can be used as a chemical probe to trap target proteins for bioactive low molecular weight compounds. In other words, compound (1) can be converted to a probe for affinity chromatography or photoaffinity or the like by incorporating a labeling group or a linker or the like into the moiety that is different from a structural moiety essential for exerting an activity of the compound, using a technique as described in J. Mass Spectrum. Soc. Jpn. Vol. 51, No. 5 2003, p 492-498 or International Publication No. WO 2007/139149 or the like.

Examples of the labeling groups or linkers or the like to be used for the chemical probe include groups listed in the group consisting of (1) to (5) as follows:

(1) protein labeling groups, such as photoaffinity labeling groups (such as a benzoyl group, a benzophenone group, an azido group, a carbonylazido group, a diaziridine group, an enone group, a diazo group, and a nitro group) and chemical affinity groups (such as ketone group in which an alpha carbon atom is replaced with a halogen atom; a carbamoyl group; an ester group; an alkylthio group; Michael receptor (such as an α,β-unsaturated ketone group and α,β-unsaturated ester group); and an oxirane group), (2) cleavable linkers such as —S—S—, —O—Si—O—, monosaccharide (such as a glucose group and a galactose group), or disaccharide (such as lactose), and oligopeptide linkers cleavable by enzymatic reactions, (3) fishing tag groups such as biotin and 3-(4,4-difluoro-5,7-dimethyl-4H-3a,4a-diaza-4-bora-s-indacen-3-yl)propionyl group, (4) radioactive label groups such as: $^{125}$I, $^{32}$P, $^{3}$H, and 14C; fluorescent label groups such as fluorescein, thodamine, dansyl, umbelliferone, 7-nitrofurazanyl, and 3-(4,4-difluoro-5,7-dimethyl-4H-3a,4a-diaza-4-bora-s-indacen-3-yl) propionyl group; chemiluminescence groups such as luciferin and luminol; and detectable markers such as lanthanoid metal ions and heavy metal ions including radium ion, or (5) groups enabling attachment to solid phase supports, such as glass beads, glass beds, microtiter plates, agarose beads, agarose beds, polystyrene beads, polystyrene beds, nylon beads, and nylon beds.

Probes prepared by incorporating a labeling group or the like selected from the group consisting of (1) to (5) as described above into compound (1) according to the methods described in the above literatures or the like can be used as chemical probes for identification of labeled proteins useful for searching for novel drug targets, for example.

EXAMPLES

Compounds according to the present invention can be produced using methods as described in, for example, the Production Examples and the Examples as described below. It should be noted that these methods are exemplary and that compounds according to the present invention are not limited to the following specific examples in any instances.

Abbreviations as used herein are as follows:
Abbreviation
SPhos: 2-dicyclohexylphosphino-2',6'-dimethoxybiphenyl
HATU: 1-[bis(dimethylamino)methylene]-1H-1,2,3-triazolo[4,5-b]pyridinium 3-oxide hexafluorophosphate
DMSO: dimethyl sulfoxide Example 1 2,6-Dichloro-N-{[3-fluoro-4-(methoxymethyl)phenyl]methyl}benzamide

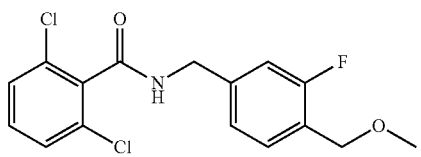 [SMILES: COCc1ccc(CNC(=O)c2c(Cl)cccc2Cl)cc1F]

To a mixture of [3-fluoro-4-(methoxymethyl)phenyl] methanamine (21 mg, 0.12 mmol) as described m Production Example 1-2 and dichloromethane (1 mL) was added RN-diisopropylethylamme (0.033 mL, 0.19 mmol) followed by 2,6-dichlorobenzoyl chloride (0.014 mL, 0.095 mmol) at room temperature and the resultant was stirred overnight at the same temperature. The reaction mixture was purified by column chromatography on silica gel (heptane:ethyl acetate=2:1) to give the title compound (30 mg, 93% yield).

$^1$H-NMR Spectrum (CDCl$_3$) δ (ppm): 3.40 (s, 3H), 4.51 (s, 2H), 4.67 (d, J=5.86 Hz, 2H), 6.07 (br. s., 1H), 7.10-7.15 (m, 1H), 7.18 (dd, J=7.81, 1.56 Hz, 1H), 7.24-7.29 (m, 1H), 7.31-7.34 (m, 2H), 7.36-7.41 (m, 1H).

Production Example 1-1
4-Bromo-2-fluoro-1-(methoxymethyl)benzene

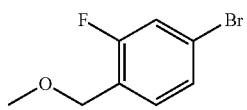

To a mixture of 4-bromo-2-fluorobenzyl bromide (10 g, 37 mmol) and methanol (37 mL) was added sodium methoxide (28% in methanol, 3.2 mL, 16 mmol) at room temperature and the resultant was stirred at the same temperature for 3 hours. Sodium methoxide (28% in methanol, 6.4 mL, 31 mmol) was further added to the reaction mixture at room temperature and the resultant was stirred at She same temperature for additional 1.5 hours. After the reaction mixture was concentrated under a reduced pressure, heptane and water were added to the residue and the resultant was neutralized with a saturated aqueous solution of ammonium chloride. After extraction with heptane, the organic layer was washed sequentially with water and brine and dried over magnesium sulfate. The solid was removed by filtration and the filtrate was evaporated to remove the solvent under a reduced pressure to give the title compound (7.6 g, 93% yield).

$^1$H-NMR Spectrum (CDCl$_3$) δ (ppm): 3.41 (s, 3H), 4.45-4.50 (m, 2H), 7.21-7.26 (m, 1H), 7.28-7.32 (m, 2H).

Production Example 1-2 [3-Fluoro-4-(methoxymethyl)phenyl]methanamine

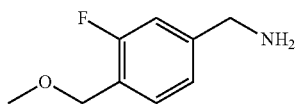

To a mixture of 4-bromo-2-fluoro-1-(methoxymethyl) benzene (2.0 g, 9.1 mmol) as described in Production Example 1-1, sodium [(1,3-dioxoisoindolin-2-yl)methyl]trifluoroborate (4.6 g, 18 mmol), palladium acetate (II) (0.31 g, 1.4 mmol), SPhos (1.4 g, 3.3 mmol), and sodium, carbonate (4.8 g, 46 mmol) were sequentially added 1,4-dioxane (34 mL) and water (17 mL) and the resultant was stirred at 110° C. under nitrogen atmosphere for 22 hours. Hydrazine hydrate (3.1 mL, 64 mmol) and 1-propanol (51 mL) were added to the reaction mixture and the resultant was stirred at 110° C. for additional 24 hours. The mixture was cooled to room temperature followed by addition of dichloromethane and brine, the reaction mixture was filtered through Celite™, and the solid was washed with dichloromethane. The organic layer of the filtrate was separated and the aqueous layer was extracted with dichloromethane (three times). All the organic layers were combined and dried over magnesium sulfate. The solid was removal by filtration and the filtrate was evaporated to remove the solvent under a reduced pressure. The residue was purified by column chromatography on NH silica gel (heptane:ethyl acetate=90:10 to 0:100 gradient). The resulting crude product was dissolved in diethyl ether and then extracted with 2 N hydrochloric acid. The resulting aqueous layer was washed sequentially with diethyl ether (once) and ethyl acetate (three times) followed by basification with 5 N sodium hydroxide aqueous solution. The solution was extracted with dichloromethane (three times) and dried over magnesium sulfate. The solid was removed by filtration and the filtrate was evaporated to remove the solvent under a reduced pressure to give the title compound (1.5 g, 94% yield).

$^1$H-NMR Spectrum (CDCl$_3$) δ (ppm): 3.40 (s, 3H), 3.87 (s, 2H), 4.51 (s, 2H). 6.99-7.14 (m, 2H). 7.35 (t, J=7.61 Hz, 1H).

Example 2 2,6-Dichloro-N-{[3,6-difluoro-4-(methoxymethyl)phenyl]methyl}benzamide

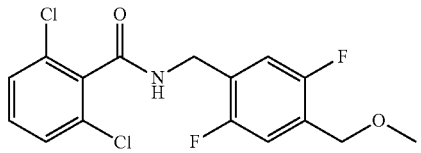 [SMILES: COCc1cc(F)c(CNC(=O)c2c(Cl)cccc2Cl)cc1F]

To a mixture of [3,6-difluoro-4-(methoxymethyl)phenyl]methanamine (23 mg, 0.12 mmol) as described in Production Example 2-3 and dichloromethane (1 mL) was added N,N-diisopropylethylamine (0.033 mL, 0.36 mmol) followed by 2,6-dichlorobenzoyl chloride (0.026 mL, 0.18 mmol) at room temperature and the resultant was stirred at the same temperature for 1 hour. The resulting reaction mixture was purified by column chromatography on silica gel (heptane:ethyl acetate=19:1 to 1:1 gradient) to give the title compound (38 mg, 88% yield).

$^1$H-NMR Spectrum (CDCl$_3$) δ (ppm): 3.42 (s, 3H), 4.48 (s, 2H), 4.67 (d, J=5.86 Hz, 2H), 6.38 (br. s, 1H), 7.07-7.16 (m, 2H), 7.18-7.28 (m, 1H), 7.29-7.34 (m, 2H).

Production Example 2-1
(4-Bromo-2,5-difluorophenyl)methanol

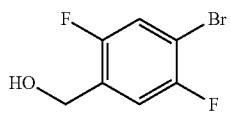

To a mixture of 4-bromo-2,5-difluorobenzoic acid (2.4 g, 10 mmol) and tetrahydrofurane (25 mL) was added borane dimethyl sulfide complex (2.5 mL, 26 mmol) at room temperature under nitrogen atmosphere. After stirred for 1.5 hours, the reaction mixture was cooled in an ice bath followed by slow dropwise addition of methanol (10 mL). After stirred at room temperature for 30 minutes, brine was added and the resultant was extracted with ethyl acetate. The organic layer was dried over magnesium sulfate. The solid was removed by filtration and the filtrate was evaporated to remove the solvent under a reduced pressure. The residue was purified by column chromatography on silica gel (heptane:ethyl acetate=9:1 to 0:10 gradient) to give the title compound (2.0 g, 96% purity (as determined by NMR), 87% yield).

$^1$H-NMR Spectrum (CDCl$_3$) δ (ppm): 1.89 (br. s, 1H). 4.72 (d, J=3.12 Hz, 2H), 7.23-7.31 (m, 2H).

Production Example 2-2
1-Bromo-2,5-difluoro-4-(methoxymethyl)benzene

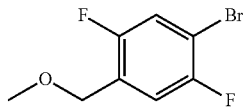

To a mixture of (4-bromo-2,5-difluorophenyl)methanol (2.0 g, 8.7 mmol) as described in Production Example 2-1 and dimethylformamide (9 mL) was added sodium hydride (60 wt %, 0.21 g, 5.2 mmol) at under ice-cooling under nitrogen atmosphere and the resultant was stirred at the same temperature for 20 minutes. Methyl iodide (2.7 mL, 44 mmol) was added under ice cooling and the resultant was stirred at the same temperature for additional 1 hour. To the resulting reaction mixture was further added sodium hydride (60 wt %, 0.21 g, 5.2 mmol) under ice cooling and the resultant was stirred for 2 hours. Water was added under ice cooling to stop the reaction and the solution was then neutralized with a saturated aqueous solution of ammonium chloride and the resultant was extracted with ethyl acetate. The resulting organic layer was washed sequentially with water and brine and dried over magnesium sulfate. The solid was removed by filtration and the filtrate was evaporated to remove the solvent under a reduced pressure. The residue was purified by column chromatography on silica gel (heptane:ethyl acetate=9:1 to 3:2 gradient) to give the title compound (1.8 g, 87% yield).

$^1$H-NMR Spectrum (CDCl$_3$) δ (ppm): 3.42 (s, 3H), 4.45 (s, 2H), 7.10-7.37 (m, 2H).

Production Example 2-3
(2,5-Difluoro-4-(methoxymethyl)phenyl)methanamine

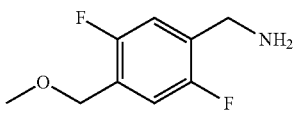

To a mixture of 1-bromo-2,5-difluoro-4-(methoxymethyl)benzene (1.8 g, 7.6 mmol) as described in Production Example 2-2, sodium [(1,3-dioxoisoindolin-2-yl)methyl]trifluoroborate (3.8 g, 15 mmol), palladium acetate (II) (0.26 g, 1.1 mmol), SPhos (1.1 g, 2.7 mmol), and sodium carbonate (4.0 g, 38 mmol) were added 1,4-dioxane (34 mL) and water (17 mL) and stirred at 110° C. under nitrogen atmosphere for 18 hours. Hydrazine monohydrate (2.6 mL, 53 mmol) and 1-propanol (43 mL) were added to the resulting reaction mixture and the resultant was stirred at 110° C. for additional 21 hours. After cooled to room temperature, dichloromethane and brine were added and the reaction mixture was filtered through Celite™ and the solid was washed with dichloromethane. The organic layer of the filtrate was separated and the aqueous layer was extracted with dichloromethane (three times). All the organic layers were combined and dried over magnesium sulfate. The solid was removed by filtration and the filtrate was evaporated to remove the solvent under a reduced pressure. The residue was dissolved in ethyl acetate and then extracted with 2 N hydrochloric acid. The resulting aqueous layer was washed with ethyl acetate (twice) followed by basification with 5 N sodium hydroxide aqueous solution. The solution was extracted with dichloromethane (three times) and dried over magnesium sulfate. The solid was removed by filtration and the filtrate was evaporated to remove the solvent under a reduced pressure. The residue was purified by column chromatography on NH silica gel (heptane:ethyl acetate=9:1 to 1:4 gradient) to give the title compound (1.2 g, 81% yield).

¹H-NMR Spectrum (CDCl₃) δ (ppm): 3.41 (s, 3H), 3.87 (s, 2H), 4.48 (s, 2H), 7.03-7.14 (m, 2H).

Example 3 2,6-Dichloro-N-[4-(methoxymethyl)benzyl]benzamide

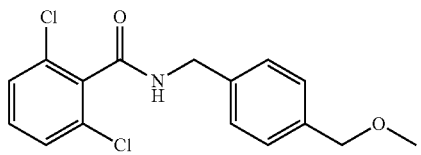 [SMILES: COCc1ccc(CNC(=O)c2c(Cl)cccc2Cl)cc1]

To a mixture of [4-(methoxymethyl)phenyl]methanamine (21 mg, 0.12 mmol) and dichloromethane (1 mL) was added triethylamine (0.040 mL, 0.29 mmol) followed by 2,6-dichlorobenzoyl chloride (0.021 mL, 0.14 mmol) at room temperature and the resultant was stirred at the same temperature for 2 hours. The reaction mixture was purified by column chromatography on silica gel (heptane:ethyl acetate=4:1 to 3:2 gradient) to give the title compound (34 mg, 93% yield).

¹NMR Spectrum (CDCl₃) δ (ppm): 3.35 (s, 3H), 4.42 (s, 2H), 4.64 (d, J=5.50 Hz, 2H), 6.09 (br. s, 1H), 7.19-7.26 (m, 1H), 7.26-7.32 (m, 4H), 7.32-7.41 (m, 2H).

Example 4 2,6-Dichloro-N-{[4-(methoxymethyl)-3-methylphenyl]methyl}benzamide

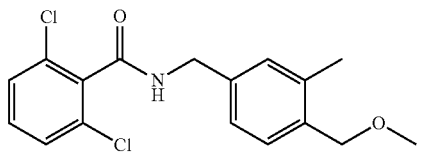

To a mixture of [4-(methoxymethyl)-3-methylphenyl]methanamine (19 mg, 0.12 mmol) as described in Production Example 4-2 and dichloromethane (1 mL) was added N,N-diisopropylethylamine (0.040 mL, 0.19 mmol) followed by 2,6-dichlorobenzoyl chloride (0.017 mL, 0.12 mmol) under ice cooling and the resultant was stirred at room temperature for 3 hours. The reaction mixture was purified by column chromatography on silica gel (heptane:ethyl acetate=2:1) and triturated with diethyl ether to give the title compound (23 mg, 59% yield).

¹NMR Spectrum (CDCl₃) δ (ppm): 2.32 (s, 3H), 3.39 (s, 3H), 4.43 (s, 2H), 4.65 (d, J=5.86 Hz, 2H), 5.95 (br. s, 1H), 7.19-7.23 (m, 2H), 7.24-7.27 (m, 2H), 7.28-7.33 (m, 3H).

Production Example 4-1 4-(Methoxymethyl)-3-methylbenzonitrile

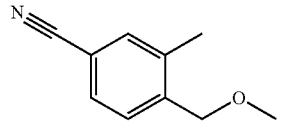

To a mixture of sodium methoxide (28% in methanol, 0.049 mL, 0.24 mmol) and methanol (1 mL) was added 4-(bromomethyl)-3-methylbenzonitrile (50 mg, 0.24 mmol) at room temperature and the resultant was stirred at the same temperature for 4 hours. Acetic acid was added to She reaction mixture at room temperature until neutralization was completed, and the mixture was evaporated to remove the solvent under a reduced pressure. The residue was purified by column chromatography on silica gel (heptane:ethyl acetate=8:1) to give the title compound (27 mg, 69% yield).

¹H-NMR Spectrum (CDCl₃) δ (ppm): 2.33 (s, 3H), 3.45 (s, 3H), 4.47 (s, 2H), 7.44-7.51 (m, 3H).

Production Example 4-2 [4-(Methyoxymethyl)-3-methylphenyl]methanamine

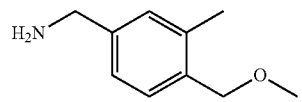

To a mixture of aluminum chloride (200 mg, 1.5 mmol) and tetrahydrofurane (3 mL) was added lithium aluminum chloride (2.5 M in tetrahydrofurane, 0.40 mL, 0.99 mmol) dropwise under ice cooling and the resultant was stirred at room temperature for 1 hour. A mixture of 4-(methoxymethyl)-3-methylbenzonitrile (53 mg, 0.33 mmol) as described in Production Example 4-1 and tetrahydrofurane (1 mL) was added dropwise to the reaction mixture under ice cooling and the resultant was stirred overnight at room temperature. To the reaction mixture was added 28% aqueous solution of ammonia under ice cooling and the resultant was stirred at room temperature for 1 hour. The reaction mixture was filtered through Celite™ and the filtrate was evaporated to remove the solvent under a reduced pressure to give the title compound (55 mg).

Mass spectrum (ESI) m/z: 166 (M+H)⁺

Example 5 2-Bromo-6-chloro-N-{[3-fluoro-4-(methoxymethyl)phenyl]methyl}benzamide

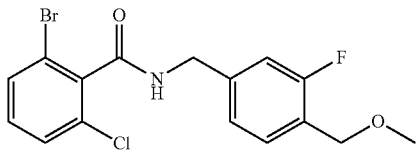

To a mixture of 2-bromo-6-chlorobenzoic acid (270 mg, 1.1 mmol) and dichloromethane (4 mL) were added sequentially N,N-diisopropylethylamine (0.39 mL, 2.3 mmol) and

[3-fluoro-4-(methoxymethyl)phenyl]methanamine (210 mg, 1.3 mmol) as described in Production Example 1-2 under ice cooling. HATU (520 mg, 1.4 mmol) was added to the reaction mixture under ice cooling and the resultant was stirred at room temperature for 3 hours. The reaction mixture was purified by column chromatography on silica gel (heptane:ethyl acetate=4:1 to 1:1 gradient) to give the title compound (300 mg, 68% yield).

$^1$H-NMR Spectrum (CDCl$_3$) δ (ppm): 3.41 (s, 3H), 4.51 (s, 2H), 4.68 (d, J=5.86 Hz, 2H). 6.01 (d, J=4.69 Hz, 1H), 7.15 (dd, J=10.54, 1.17 Hz, 1H), 7.17-7.22 (m, 2H), 7.35-7.42 (m, 2H), 7.48-7.51 (m, 1H), 7.48-7.51 (m, 1H).

Example 6 2-Chloro-N-{[3-fluoro-4-(methoxymethyl)phenyl]methyl}benzamide

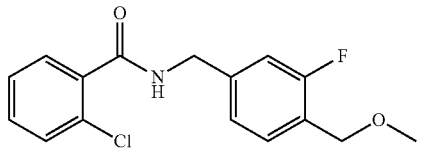 [SMILES: COCc1ccc(CNC(=O)c2ccccc2Cl)cc1F]

To a mixture of [3-fluoro-4-(methoxymethyl)phenyl]methanamine (30 mg, 0.18 mmol) as described in Production Example 1-2, N,N-diisopropylethylamine (0.061 mL, 0.36 mmol), and dichloromethane (1 mL) was added 2-chlorobenzoyl chloride (0.022 mL, 0.18 mmol) at room temperature and the resultant was stirred at the same temperature for 2 hours. The reaction mixture was purified by column chromatography on silica gel (heptane:ethyl acetate=3:2) to give the title compound (47 mg, 86%, yield).

$^1$H-NMR Spectrum (CDCl$_3$) δ (ppm): 3.41 (s, 3H), 4.51 (s, 2H), 4.66 (d, J=5.86 Hz, 2H), 6.54 (br. s., 1H), 7.09 (dd, J=10.54, 1.56 Hz, 1H), 7.16 (dd, J=7.81, 1.56 Hz, 1H), 7.31-7.43 (m, 4H), 7.69-7.73 (m, 1H).

Example 7 2-Bromo-N-{[3-fluoro-4-(methoxymethyl)phenyl]methyl}benzamide

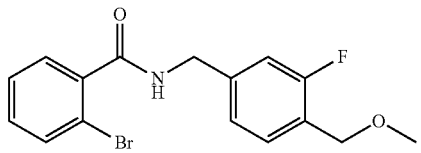 [SMILES: COCc1ccc(CNC(=O)c2ccccc2Br)cc1F]

To a mixture of [3-fluoro-4-(methoxmethyl)phenyl]methanamine (30 mg, 0.18 mmol) as described in Production Example 1-2, N,N-diisopropylethylamine (0.061 mL, 0.36 mmol), and dichloromethane (1 mL) was added 2-bromobenzoyl chloride (0.023 mL, 0.18 mmol) at room temperature and the resultant was stirred at the same temperature for 2 hours.

The reaction mixture was purified by column chromatography on silica gel (heptane:ethyl acetate=3:2) to give the title compound (49 mg, 78%, yield).

$^1$H-NMR Spectrum (CDCl$_3$) δ (ppm): 3.41 (s, 3H), 4.5 (s, 2H), 4.65 (d, J=5.86 Hz, 2H), 6.31 (br. s., 1H), 7.10 (dd, J=0.54, 1.56 Hz, 1H), 7.17 (dd, J=7.81, 1.56 Hz, 1H), 7.26-7.31 (m, 1H), 7.34-7.38 (m, 1H), 7.38-7.41 (m, 1H), 7.58 (ddd, J=9.18, 7.81, 1.37 Hz, 2H).

Example 8 2-Bromo-6-fluoro-N-{[3-fluoro-4-(methoxymethyl)phenyl]methyl}benzamide

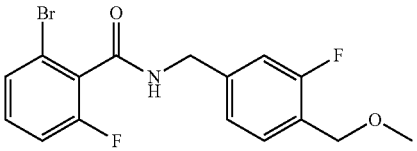

To a mixture of 2-bromo-6-fluorobenzoic acid (15 mg, 0.068 mmol) and N,N-dimethylformamide (0.5 mL) were sequentially added N,N-diisopropylethylamine (0.029 mL, 0.17 mmol) and [3-fluoro-4-(methoxymethyl)phenyl]methanamine (17 mg, 0.10 mmol) as described in Production Example 1-2 under ice cooling. HATU (39 mg, 0.10 mmol) was added to the reaction mixture under ice cooling and the resultant was stirred overnight at room temperature. Water was added to the reaction mixture and the resultant was extracted with ethyl acetate. The organic layer was washed sequentially with water and brine and evaporated to remove the solvent under a reduced pressure. The residue was purified by column chromatography on silica gel (heptane:ethyl acetate=3:1 to 3:2 gradient) to give the title compound (20 mg, 80% yield).

$^1$H-NMR Spectrum (CDCl$_3$) δ (ppm): 3.41 (s, 3H), 4.51 (s, 2H), 4.67 (d, J=6.25 Hz, 2H), 6.07 (br. s., 1H), 7.07-7.14 (m, 2H), 7.18 (d, J=8.20 Hz, 1H), 7.22-7.29 (m, 1H), 7.37-7.42 (m, 2H).

Example 9 2-Chloro-N-{[3-fluoro-4-(methoxymethyl)phenyl]methyl}-6-(methoxymethyl)benzamide

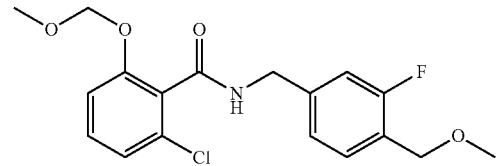

To a mixture of methyl 2-chloro-6-(methoxymethyl)benzoate (220 mg, 0.95 mmol) as described in Production Example 9-1, methanol (0.6 mL), and water (0.6 mL) was added lithium hydroxide monohydrate (40 mg, 0.95 mmol) at room temperature and the resultant was stirred overnight at 50° C., The reaction mixture was evaporated to remove the solvent under a reduced pressure. To a mixture of the residue and N,N-dimethylformamide (5 mL) were sequentially added N,N-diisopropylethylamine (0.40 mL, 2.4 mmol) and [3-fluoro-4-(methoxymethyl)phenyl]methanamine (240 mg, 1.4 mmol) as described in Production Example 1-2 under ice cooling. HATU (540 mg, 1.4 mmol) was added to the reaction mixture under ice cooling and lite resultant was stirred at room temperature for 3 hours. Water was added to the reaction mixture and the resultant was extracted with ethyl acetate. The organic layer was washed sequentially with water and brine and evaporated to remove the solvent under a reduced pressure. The residue was purified by column chromatography on silica gel (heptane:ethyl acetate=7:3 to 1:1 gradient) to give the title compound (54 mg, 16% yield).

¹H-NMR Spectrum (CDCl₃) δ (ppm): 3.41 (s, 3H), 3.46 (s, 3H), 4.51 (s, 2H), 4.69 (d, J=6.25 Hz, 2H), 5.22 (s, 2H), 6.05 (br. s, 1H), 7.04-7.10 (m, 2H), 7.15-7.28 (m, 3H), 7.38 (t, J=7.61 Hz, 1H).

Production Example 9-1 Methyl 2-chloro-6-(methoxymethyl)benzoate

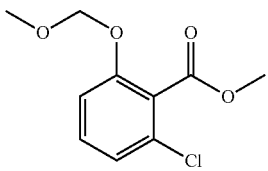

To a mixture of methyl 2-chloro-6-hydroxybenzoate (970 mg, 5.2 mmol) and N,N-dimethylformamide (10 mL) were sequentially added potassium carbonate (1.1 g, 7.8 mmol) and methoxymethyl chloride (0.41 mL, 5.4 mmol) under ice cooling and the resultant was stirred at room temperature for 3 hours. Potassium carbonate (0.36 g, 2.6 mmol) and methoxymethyl chloride (0.20 mL, 2.6 mmol) were sequentially added to the reaction mixture under ice cooling and the resultant was stirred overnight at room temperature. Water was added to the reaction mixture and the resultant was extracted with ethyl acetate. The organic layer was washed sequentially with water and brine and evaporated to remove the solvent under a reduced pressure. The residue was purified by filtration through NH silica gel to give the title compound (1.2 g, 97% yield).

¹H-NMR Spectrum (CDCl₃) δ (ppm): 3.47 (s, 3H) 3.46-3.48 (m, 3H) 3.95 (s, 3H) 5.19 (s, 2H) 7.03-7.06 (m, 1H) 7.06-7.09 (m, 1H) 7.24-7.29 (m, 1H).

Example 10 2-Chloro-6-fluoro-N-{[3-fluoro-4-(methoxymethyl)phenyl]methyl}benzamide

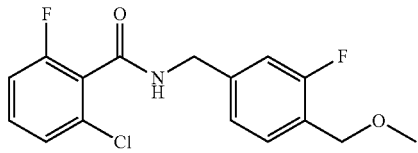

To a mixture of [3-fluoro-4-(methoxymethyl)phenyl]methanamine (16 mg, 0.095 mmol) as described in Production Example 1-2 and dichloromethane (0.5 mL) were added N,N-diisopropylethylamine (0.033 mL, 0.19 mmol) and 2-chloro-6-fluorobenzoyl chloride (0.013 mL, 0.095 mmol) under ice cooling and the resultant was stirred at room temperature for 3 hours. The reaction mixture was purified by column chromatography on silica gel (heptane:ethyl acetate=3:1 to 3:2 gradient) to give the title compound (32 mg, a quantitative yield).

¹H-NMR Spectrum (CDCl₃) δ (ppm): 3.40 (s, 3H), 4.51 (s, 2H), 4.67 (d, J=6.25 Hz, 2H), 6.11 (br. s., 1H), 7.05 (td, J=8.49, 0.98 Hz, 1H), 7.10 (d, J=10.54 Hz, 1H). 7.16 (d, J=7.81 Hz, 1H), 7.21-7.24 (m, 1H), 7.29-7.35 (m, 1H), 7.39 (t, J=7.8 Hz, 1H).

Example 11 N-{[3-Fluoro-4-(methoxymethyl)phenyl]methyl}-2,6-dimethylbenzamide

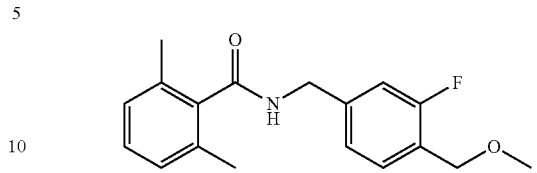

To a mixture of 2,6-dimethyl benzoic acid (30 mg, 0.20 mmol) and N,N-dimethylformamide (0.3 mL) were sequentially added N,N-diisopropylethylamine (0.068 mL, 0.40 mmol) and [3-fluoro-4-(methoxymethyl)phenyl]methanamine (34 mg, 0.20 mmol) as described in Production Example 1-2 under ice cooling. HATU (99 mg, 0.26 mmol) was added to the reaction mixture under ice cooling and the resultant was stirred at room temperature for 3 hours. Water was added to the reaction mixture and the resultant was extracted with ethyl acetate. The organic layer was washed sequentially with water and brine and evaporated to remove the solvent under a reduced pressure. The residue was purified by column chromatography on silica gel (heptane:ethyl acetate=75:25 to 65:35 gradient) to give the title compound (42 mg, 70% yield).

¹H-NMR Spectrum (CDCl₃) δ (ppm): 2.31 (s, 6H), 3.41 (s, 3H), 4.51 (s, 2H), 4.63 (d, J=5.86 Hz, 2H), 5.94 (br. s., 1H), 7.01 (d, J=8.20 Hz, 2H), 7.08 (dd, J=10.35, 1.76 Hz, 1H), 7.13-7.18 (m, 2H), 7.39 (t, J=7.61 Hz, 1H).

Example 12 2-Chloro-N-[3-fluoro-4-(methoxymethyl)benzyl]-6-isopropylbenzamide

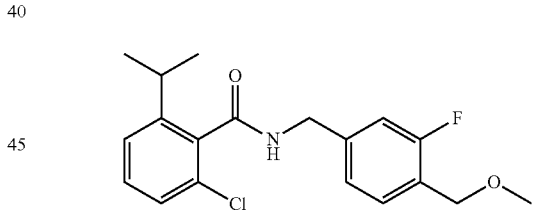

To a mixture of 2-chloro-N-[3-fluoro-4-(methoxymethyl)benzyl-6-(prop-1-en-2-yl)]benzamide (20 mg, 0.059 mmol) as described in Production Example 12-1, methanol (1 mL), and tetrahydrofurane (0.5 mL) was added palladium-fibroin (25 mg, 0.0059 mmol) and the resultant was stirred overnight under hydrogen atmosphere at room temperature. Hydrogen in the reaction system was replaced with nitrogen and the reaction mixture was filtered through filter paper. The filtrate was evaporated to remove the solvent under a reduced pressure and the residue was purified by chromatography on silica gel (heptane:ethyl acetate=3:1 to 2:1 gradient) to give the title compound (18 mg, 87% yield).

¹H-NMR Spectrum (CDCl₃) δ (ppm): 1.22 (d, J=6.70 Hz, 6H), 3.04 (dt, J=13.60, 6.95 Hz, 1H), 3.39 (s, 3H), 4.49 (s, 2H), 4.64 (d, J=5.86 Hz, 2H), 5.95 (br. s., 1H). 7.05-7.12 (m, 1H), 7.16 (dd, J=7.95, 1.22 Hz, 1H), 7.20 (td, J=6.73, 1.22 Hz, 1H), 7.22-7.30 (m, 2H), 7.37 (t, J=7.64 Hz, 1H).

Production Example 12-1 2-Chloro-N-[3-fluoro-4-(methoxymethyl)benzyl-6-(prop-1-en-2-yl)]benzamide

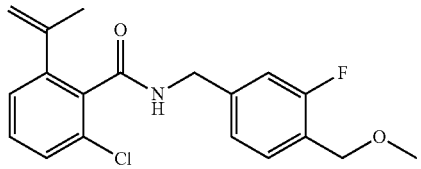 [SMILES: C=C(C)c1cccc(Cl)c1C(=O)NCc1ccc(COC)c(F)c1]

To a mixture of 2-bromo-6-chloro-N-[3-fluoro-4-(methoxymethyl)benzyl]benzamide (30 mg, 0.078 mmol) as described in Example 5, sodium carbonate (12 mg, 0.12 mmol), tetrakis(triphenylphosphine)palladium(0) (4.5 mg, 0.0039 mmol) were sequentially added 1,4-dioxane (0.6 mL), pure water (0.2 mL), and 2-isopropenyl-4,4,5,5-tetramethyl-1,3,2-dioxaborolane (19 mL, 0.10 mmol) and the resultant was stirred with heating at 100° C. overnight. The reaction mixture was filtered through Celite™ and the filtrate was evaporated to remove the solvent under a reduced pressure. The residue was purified by thin layer chromatography on silica gel (heptane:ethyl acetate=2:1) to give the title compound (23 mg, 87% yield).

$^1$H-NMR Spectrum (CDCl$_3$) δ (ppm), 2.04 (s, 3H), 3.38 (s, 3H), 4.49 (s, 2H), 4.58 (d, J=6.11 Hz, 2H), 5.02 (br. s., 1H), 5.16 (t, J=1.53 Hz, 1H), 5.95 (br. s, 1H), 7.07 (d, J=1.39 Hz, 1H), 7.09-7.16 (m, 2H), 7.21-7.32 (m, 2H). 7.32-7.42 (m, 1H).

Example 13 2,6-Difluoro-N-{[3-fluoro-4-(methoxymethyl)phenyl]methyl}benzamide

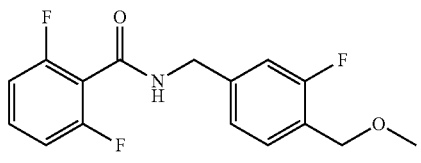 [SMILES: COCc1ccc(CNC(=O)c2c(F)cccc2F)cc1F]

To a mixture of [3-fluoro-4-(methoxymethyl)phenyl]methanamine (32 mg, 0.19 mmol) as described in Production Example 1-2 and dichloromethane (2 mL) were added N,N-diisopropylethylamine (0.033 mL, 0.19 mmol) and 2,6-difluorobenzoyl chloride (0.054 mL, 0.32 mmol) under ice cooling and the resultant was stirred at room temperature for 3 hours. The reaction mixture was purified by column chromatography on silica gel (heptane:ethyl acetate=4:1 to 1:1 gradient) to give the title compound (46 mg, 93% yield).

1H-NMR Spectrum (CDCl$_3$) δ (ppm): 3.39 (s, 3H), 4.49 (s, 2H), 4.64 (d, J=5.89 Hz, 2H), 6.29 (br. s, 1H), 6.91-6.98 (m, 2H), 7.05 (dd, J=10.65, 1.59 Hz, 1H), 7.13 (dd, J=7.93, 1.59 Hz, 1H), 7.32-7.41 (m, 2H).

Comparative Example 1 N-[(2H-1,3-Benzodioxol-5-yl)methyl]-2,6-dichlorobenzamide (Alda-1) was used directly from a commercially available compound

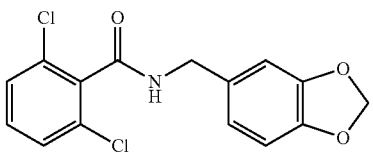 [SMILES: O=C(NCc1ccc2c(c1)OCO2)c1c(Cl)cccc1Cl]

Comparative Example 2 2,6-dichloro-N-[(2,3-dihydro-1,4-benzodioxin-6-yl)methyl]benzamide

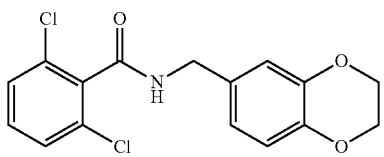 [SMILES: O=C(NCc1ccc2c(c1)OCCO2)c1c(Cl)cccc1Cl]

To a mixture of 2,3-dihydro-1,4-benzodioxin-6-yl)methylamine (50 mg, 0.30 mmol) and dichloromethane (1 mL) were added N,N-diisopropylethylamine (0.11 mL, 0.61 mmol) and 2,6-dichlorobenzoyl chloride (0.043 mL, 0.30 mmol) under ice cooling and the resultant was stirred at room temperature for 3 hours. The reaction mixture was purified by column chromatography on silica gel (heptane:ethyl acetate=2:1) to give the title compound (94 mg, 92% yield).

$^1$H-NMR Spectrum (CDCl$_3$) δ (ppm): 4.24 (s, 4H), 4.57 (d, J=5.47 Hz, 2H), 5.94 (br. s, 1H), 6.81-6.92 (m, 3H), 7.21-7.33 (m, 3H).

Comparative Example 3 2,6-Dichloro-N-(4-fluoro-3-methoxybenzyl)benzamide

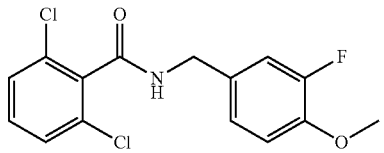 [SMILES: COc1ccc(CNC(=O)c2c(Cl)cccc2Cl)cc1F]

To a mixture of 3-fluoro-4-methoxybenzylamine (28.9 mg, 0.19 mmol) and dichloromethane (1 mL) was added triethylamine (0.040 mL, 0.29 mmol) followed by 2,6-dichlorobenzoyl chloride (0.021 mL, 0.14 mmol) under ice cooling and the resultant was stirred at room temperature for 1 hour. The reaction mixture was filtered through Celite™ and the filtrate was evaporated to remove the solvent under a reduced pressure. The residue was triturated with heptane/ethyl acetate (1:1) to give the title compound (47 mg, 60% yield).

$^1$H-NMR Spectrum (DMSO-d$_6$) δ (ppm): 3.78 (s, 3H), 4.37 (d, J=6.11 Hz, 2H), 7.07-7.14 (m, 1H), 7.14-7.20 (m, 1H), 7.37-7.43 (m, 1H), 7.47 (s, 1H), 7.48 (s, 1H), 9.07-9.17 (m, 1H).

Test Example 1

(Effects of Compounds on the Acetaldehyde Oxidation Rate by Aldehyde Dehydrogenase 2 (ALDH2))

Effects of compounds on the acetaldehyde oxidation rate by aldehyde dehydrogenase 2 (ALDH2) were evaluated using a method known in the art. Specifically, the test was performed using a commercially available kit, PicoProbe™ Aldehyde dehydrogenase Activity Assay Kit (from BioVision Inc.) in accordance with the product's instruction. Reagents as described below were sequentially added to each well in a 384-well plate with a pipette.

1. 10 µL of the commercially available ALDH2 enzyme (from ATGen Inc.) dissolved in ALDH assay Buffer so as to obtain a concentration of 1 µg/mL.
2. 10 µL, of 30 µM or 3 µM compound solution (containing 3% DMSO) prepared with ALDH assay Buffer
3. 10 ηL of Reaction mix consisting of 7.82 µL of ALDH assay Buffer, 0.55 µL of PicoProbe, 0.27 µL of Substrate Mix, and 1.36 µL of Acetaldehyde Before addition of 3, the plate was incubated at room temperature for 5 minutes. After addition of 3, fluorescence was determined using EnVision 2101 Multilabel Reader (from PerkinElmer Inc.) at room, temperature over 60 minutes. The measurements were taken at interval of 2 minutes.

Fluorescence was detected at an excitation wavelength of 535 nm and an emission wavelength of 587 nm.

Table 1 lists the oxidation rates when the compounds are added, in which the rates are calculated on the basis of the assumption that the acetaldehyde oxidation rates in the absence of the compounds are 100. The rate for Comparative Example 1 compound was normalized to a value of "175" for 10 µM of the compound concentration while the rate for Comparative Example 1 compound was normalized to a value of "137" for 1 µM of the compound concentration. The results indicated that the compounds according to the present invention increased the acetaldehyde oxidation rate in a manner similar to Comparative Example compounds.

TABLE 1

| | Compound Concentration | |
|---|---|---|
| | 10 µM | 1 µM |
| Example 1 | 179 | 138 |
| Example 2 | 168 | 125 |
| Example 3 | 156 | 117 |
| Example 4 | 175 | 136 |
| Example 5 | 168 | 129 |
| Example 6 | 148 | 108 |
| Example 7 | 156 | 119 |
| Example 8 | 165 | 128 |
| Example 9 | 170 | 120 |
| Example 10 | 168 | 125 |
| Example 11 | 156 | 117 |
| Example 12 | 175 | 136 |
| Example 13 | 143 | 114 |
| Comparative Example 1 | 175 | 137 |
| Comparative Example 2 | 164 | 125 |
| Comparative Example 3 | 165 | 135 |

Test Example 2

(Comparison of Amounts of Produced Reactive Metabolites)

Ability of compounds to produce reactive metabolites was evaluated, using the method as described below. Cytochrome P450 (CYP) dependent metabolism was initiated, by adding 1 mg/mL human liver microsome, 0.2 mmol/L compound, and 0.1 mmol/L RI-labeled capture agent, and lastly 1 mmol/L NADPH to 100 mM phosphate buffer (pH 7.4). After incubation at 37° C. for 60 minutes, the reaction mixture (0.1 mL) and an equal volume of acetonitrile were added to stop the metabolic reaction. After 0.8 mL of water was added to the supernatant from centrifugation, 0.5 mL of the resulting solution was injected into HPLC connected to a radio detector and a covalent complex between the reactive metabolite and Relabeled capture agent was quantitatively analyzed for its RI intensity.

The results as shown in Table 2 indicated that compounds according to the present invention produced a smaller amount of reactive metabolites than clozapine, which is known to induce serious blood toxicity and hepatotoxicity via production of reactive metabolites, and Comparative Example compounds.

TABLE 2

| | Reactive Metabolites (% of clozapine) |
|---|---|
| Example 1 | 8 |
| Example 2 | 15 |
| Example 3 | 10 |
| Example 4 | 7 |
| Example 5 | 5 |
| Example 6 | 8 |
| Example 7 | 24 |
| Example 8 | 10 |
| Example 9 | 20 |
| Example 10 | 10 |
| Example 11 | 34 |
| Example 12 | 7 |
| Example 13 | 15 |
| Clozapine | 100 |
| Comparative Example 1 | 90 |
| Comparative Example 2 | 147 |
| Comparative Example 3 | 263 |

Test Example 3

(Suppressive Effect of Pain Induced by Carrageenan)

This experiment was earned out with reference to Science Translational Medicine 6, 251 r118 (2014). Male C57 BL/6J mice (Charles River Japan) of 7-week-old were used. Carrageenan was subcutaneously administered to the mouse by intraplantar injection of the left hind paw to induce mechanical allodynia in the footpad. Mechanical stimulus-evoked withdrawal response at 180 min after the induction was assessed by applying a von Frey filament (ascending bending force 0.16 g) to the footpad, of the hind paw. The filament was perpendicularly applied to the footpad so that the filament was bent for 6 second. The withdrawal response was scored in three stages (0: no response or startle response (moving paw without lifting); 1: lifting of paw; 2: licking or shaking of paw). The mouse was stimulated ten times and the sum of the scores of the ten stimulation (withdrawal score) was calculated.

The compound of Example 1 was dissolved in DMSO/5% glucose solution for injection (1:1 by volume ratio). The compound was subcutaneously administered to the dorso-cervical site of the mouse at a dose of 12 mg/kg (no compound in vehicle-treated group) and at a volume of 5 mL/kg three times in total: 15 min before the carrageenan injection, and 30 min and 150 min after the carrageenan injection. Carrageenan was dissolved in a physiological saline to prepare a 1.5% solution, and it was subcutaneously administered to the footpad of the hind paw at 7 μL/body.

Wilcoxon rank sum test was used to compare the vehicle-treated group and the Example 1-treated group. The significance level was calculated as 5%, divided into less than 5% ($p<0.05$) and less than 1% ($p<0.01$). For the significant difference test, a commercially available statistical program SAS SYSTEM (SAS Software Release 9.1.3; SAS Institute Japan Ltd) was used. As shown in Table 3, it was shown that the compound according to the present invention suppresses pain induced by carrageenin.

TABLE 3

| Group | Vehicle | Example 1 |
|---|---|---|
| Number of animals | 5 | 5 |
| Total pain-related score | | |
| Time after carrageenan induction (min) | | |
| Pre | 1.8 ± 0.2 | 1.6 ± 0.2 |
| 180 | 15.6 ± 1.4 | 6.8 ± 1.0** |

Each value shows mean ± S. E.
Pre: Before induction
Significantly different from vehicle group (**$p < 0.01$)

What is claimed is:

1. A compound selected from:
   (1) 2,6-dichloro-N-{[3-fluoro-4-(methoxymethyl)phenyl]methyl}benzamide,
   (2) 2,6-dichloro-N-{[3,6-difluoro-4-(methoxymethyl)phenyl]methyl}benzamide,
   (3) 2,6-dichloro-N-[4-(methoxymethyl)benzyl]benzamide,
   (4) 2,6-dichloro-N-{[4-(methoxymethyl)-3-methylphenyl]methyl}benzamide,
   (5) 2-bromo-6-chloro-N-{[3-fluoro-4-(methoxymethyl)phenyl]methyl}benzamide,
   (6) 2-chloro-N-{[3-fluoro-4-(methoxymethyl)phenyl]methyl}benzamide,
   (7) 2-bromo-N-{[3-fluoro-4-(methoxymethyl)phenyl]methyl}benzamide,
   (8) 2-bromo-6-fluoro-N-{[3-fluoro-4-(methoxymethyl)phenyl]methyl}benzamide,
   (9) 2-chloro-N-{[3-fluoro-4-(methoxymethyl)phenyl]methyl}-6-(methoxymethyl)benzamide,
   (10) 2-chloro-6-fluoro-N-{[3-fluoro-4-(methoxymethyl)phenyl]methyl}benzamide,
   (11) N-{[3-fluoro-4-(methoxymethyl)phenyl]methyl}-2,6-dimethylbenzamide,
   (12) 2-chloro-N-[3-fluoro-4-(methoxymethyl)benzyl]-6-isopropylbenzamide, and
   (13) 2,6-difluoro-N-{[3-fluoro-4-(methoxymethyl)phenyl]methyl}benzamide or a pharmaceutically acceptable salt thereof.

2. 2,6-dichloro-N-{[3-fluoro-4-(methoxymethyl)phenyl]methyl}benzamide represented by the formula:

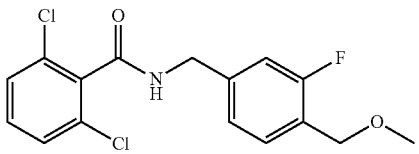

or a pharmaceutically acceptable salt thereof.

3. 2,6-dichloro-N-{[4-(methoxymethyl)-3-methylphenyl]methyl}benzamide represented by the formula:

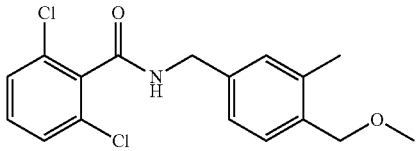

or a pharmaceutically acceptable salt thereof.

4. 2-bromo-6-fluoro-N-{[3-fluoro-4-(methoxymethyl)phenyl]methyl}benzamide represented by the formula:

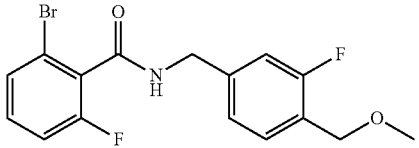 [SMILES: COCc1ccc(CNC(=O)c2c(F)cccc2Br)cc1F]

or a pharmaceutically acceptable salt thereof.

5. A pharmaceutical composition comprising the compound or a pharmaceutically acceptable salt thereof according to claim 1 and a pharmaceutically acceptable additive.

* * * * *